United States Patent [19]

Greco et al.

[11] 3,956,178

[45] May 11, 1976

[54] THREE-COMPONENT METATHESIS CATALYSTS

[75] Inventors: Alberto Greco; Franco Pirinoli; Gino Dall'Asta, all of Milan, Italy

[73] Assignee: Montedison S.p.A., Milan, Italy

[22] Filed: Feb. 13, 1974

[21] Appl. No.: 442,238

[30] Foreign Application Priority Data
Feb. 14, 1973  Italy .................................. 20370/73

[52] U.S. Cl. .......................... 252/429 B; 260/683 D
[51] Int. Cl.$^2$ ........................................... B01J 31/14
[58] Field of Search ............... 252/429 B; 260/683 D

[56] References Cited
UNITED STATES PATENTS

| | | | |
|---|---|---|---|
| 3,116,274 | 12/1963 | Boehm et al. ................ | 252/429 B X |
| 3,449,310 | 6/1969 | Dall'Asta et al. ............ | 252/429 B X |
| 3,558,518 | 1/1971 | Zeuch ............................. | 252/429 B |
| 3,784,629 | 1/1974 | Maly et al. .................... | 252/429 B X |
| 3,790,543 | 2/1974 | Lehnert et al. ................ | 252/429 B X |
| 3,798,175 | 3/1974 | Streck et al. .................. | 252/429 B |

*Primary Examiner*—Patrick P. Garvin

[57] ABSTRACT

New three-component metathesis catalysts prepared from a tungsten compound, an organic ligand and an organometallic compound of a metal belonging to Group I to IV of the Mendelyeev Periodic System are disclosed. More particularly, the disclosed catalysts are prepared from a tungsten oxychloride, an organic ligand containing a nitrile or ester group, and an organic aluminum compound.

9 Claims, No Drawings

THREE-COMPONENT METATHESIS CATALYSTS

THE PRIOR ART

Metathesis catalysts prepared from tungsten halides containing oxygenated activators are known. Those catalysts are presently the most active known catalysts in the metathesis of aliphatic olefins, resulting in the dismutation of the latter, and in the metathesis of cyclic olefins, which results in the formation of polyalkenamers.

Said known catalysts are prepared in two steps. In the first step, the tungsten halide is reacted with the oxygenated activator in the presence of the aliphatic or cyclic olefin; in the second step the organic aluminum compound is added.

The disadvantage is that the intermediates which are formed in the first step must be soluble and stable for a rather long time and this does not always occur. Often the intermediates undergo rapid decomposition with the precipitation of insoluble products which are not catalytically active.

The problem existing in the art, therefore, has been the need for metathesis catalysts which are at least as active as the known catalysts but which do not involve the problem of rapid decomposition of intermediates and the precipitation of insoluble products which are not catalytically active.

THE PRESENT INVENTION

One object of this invention is to solve the problem heretofore existing in the art by providing new metathesis catalysts which are at least as active as the known metathesis catalysts referred to hereinabove but which do not have the disadvantages of those catalysts.

That and other objects are accomplished by the present invention which provides new metathesis catalysts which are prepared by mixing a catalyst-forming component (A) which is the reaction product of (a) a tungsten compound containing a W = O bond and at least two W — Cl bonds, such as, for instance $WOCl_4$, with (b) an organic ligand containing a nitrile or ester group, with a second catalyst-forming component (B) which is an organometallic compound of a metal belonging to one of Groups I to IV of the Mendelyeev Periodic System.

The new metathesis catalysts of the present invention have the advantage that the catalyst-forming component or complex (A) which is the reaction product of the tungsten compound as specified and the organic ligand is completely soluble in the reaction medium in which it is formed and there is no precipitation of insoluble, catalytically inactive products, if the reaction mixture in which the complex is formed, or the complex isolated from the reaction medium is held for indefinite periods of time, even if the temperature of such holding is room temperature, and provided that the complex is not exposed to air or humidity, prior to use.

The two catalyst component-forming substances (a) and (b) are reacted in an inert atmosphere, such as dry nitrogen, in a reaction medium consisting of hydrocarbons, e.g., benzene or n-heptane, or of chlorinated hydrocarbons, such as, e.g., chlorobenzene, at temperatures ranging from −50° C to +50° C, preferably from 0° C to +30° C.

The molar ratio of (a) to (b) is in the range from 1:0.5 to 1:10, preferably from 1:0.9 to 1:1.5. The reaction is continued until the tungsten compound is solubilized.

When the tungsten compound is $WOCl_4$, the complex which is formed by the reaction of (a) and (b) has the structure $WOCl_4$ R, in which R is a nitrile or ester group.

The mixture in which the complex is formed may be used, as such, as one component of the final metathesis catalyst. That is, the reaction mixture comprising the complex may be introduced, as such, into the aliphatic or cyclic olefin to be metathesized and an organometallic compound of a metal belonging to one of Groups I to IV of the Mendelyeev Periodic System added as catalyst-forming component (B).

Alternatively, the complex formed by the reaction of (a) and (b) may be isolated from the reaction mixture in which it is formed and mixed with the aliphatic or cycloolefin to be metathesized, after which the organometallic compound of the Groups I to IV metal, [Catalyst-forming component (B)] is added.

The useful compounds of the Groups I to IV metals include: $Al(C_2H_5)_3$, $Al(C_2H_5)_2Cl$, $Al_2(C_2H_5)_3Cl_3$, $AlC_2H_5Cl_2$, $Al(isobutyl)Cl_2$, $LiAl(C_2H_5)_4$, tin tetraethyl and lithium butyl.

The (a) : (B) ratio employed is in the range of from 1:1 to 1:5, preferably 1:1.8 to 1:2.2.

Examples of organic ligands which may be employed according to this invention are phthalodinitrile, adiponitrile and ethyl phthalate.

The complex having the structure $WOCl_4$ R wherein R is a nitrile or ester yields chelates, if R contains two nitrile or ester groups. For instance, when R is adiponitrile, the complex is a chelate having the following structure:

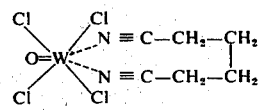

The catalysts of this invention promote the metathesis of the olefins and cycloolefins also when the molar ratio of olefin to W ranges from at least 500 : 1 to 10,000:1 and more. In the case of cyclopentene, a polypentenamer having a high molecular weight and a predominant transstructure of the double bonds is obtained.

The reaction conditions for the metathesis of olefins and cycloolefins are those already known. For example, the preparation of polyalkenamers by metathesis of cycloolefins is carried out at temperatures between −80°C and +100°C.

The metathesis is carried out in a liquid phase consisting of the reaction medium (hydrocarbon or chlorinated hydrocarbon solvent) as the diluent, or in a diluent consisting of the monomer to be metathesized.

In general the metathesis of olefins by means of the catalysts of this invention is carried out at a temperature in the range of −50°C to +50°C.

The olefins which can be metathesized using the catalysts of this invention are those having from 2 to 30 carbon atoms.

The aliphatic olefins that are preferably metathesized are for example pentene-2, butene-2, hexene-2, 2.7-dimethyl-octene-2, etc. Specially preferred is pentene-2.

The cyclic olefins that are preferably used in the metathesis reaction and lead to the formation of polyalkenamers are cyclopentene, cis-cyclooctene, cycloheptene and cyclododecene. Specially preferred is cyclopentene.

Among the advantages of this invention is the fact that, in contrast to the process by which the most effective metathesis catalysts of the prior art are prepared, the tungsten compound which is used in the preparation of the present catalysts is an oxyhalide which comprises a built-in activator and on reaction with the organic ligand forms a complex which is completely soluble in the hydrocarbon or chlorinated hydrocarbon in which the reaction is carried out and which remains stable indefinitely in the reaction mixture, even at room temperature and provided it is not exposed to air or humidity prior to use.

The following examples are given to illustrate this invention and are not intended to be limiting.

EXAMPLE 1

Preparation of $WOCl_4$ . phthalodinitrile.
4.3 g of $WOCl_4$ = 12.5 millimoles
60 ml of anhydrous benzene distilled on $CaH_2$
1.6 g of phthalodinitrile = 12.5 millimoles
are introduced into a 100 ml necked test tube, in a nitrogen atmosphere. After a 5-hour reaction at room temperature, a little amount of a yellow precipitate is filtered, which is then washed with petroleum ether. Petroleum ether is admixed to the mother solution, which is cooled down to 0°C. Needle-like crystals precipitate from this solution and are then dried by means of a mechanical pump. Yield = 3.7 g (66% of the calculated yield). The compound has the following structure:

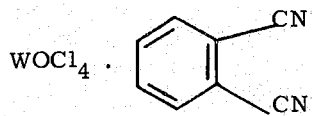

Both the elemental analysis and the infrared spectrum proves the structure given.

Infrared spectrum : 2280 (m) (C = N); 1575 (w) ; 1495 (w) ; 1307 (w) ; 1215 (w) ; 1035 (w) ; 1005 (s) ; 856 (w) ; 762 (s) ; 687 (s) (W = O)cm$^{-1}$.

The compound is completely soluble in aliphatic, cycloaliphatic, aromatic and chlorinated hydrocarbons, such as n-heptane, cyclohexane, cyclopentene, benzene, chlorobenzene. The resulting solutions do not show signs of decomposition even after a 1-month period of storage at room temperature.

EXAMPLE 2

Preparation of $WOCl_4$ . ethyl phthalate.
5.65 g of $WOCl_4$ = 16.5 millimoles
80 ml of petroleum ether
3.28 ml of diethyl phthalate = 16.5 millimoles
are introduced into a 100 ml necked test tube, in a nitrogen atmosphere, at room temperature.

Reaction is carried on for 4 hours at room temperature under continuous stirring. Then a small amount of insoluble material is filtered and the mother solution is cooled to −30°C. A yellow compound separates from it in the form of crystals, which are dried under vacuum by means of a mechanical pump.

Yield = 4.1 g(44% of the calculated value).

The compound has the following structure:

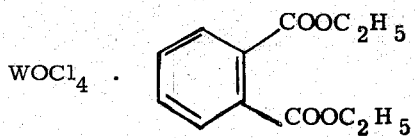

That structure is established by both the elemental analysis and the infrared spectrum.

Infrared spectrum: 1732 (s) − 1708 (s) (not complexed C = O); 1630 (vs) (complexed C = O); 1595 (m); 1576 (m); 1485 (m); 1397 (m) 1376 (s); 1363 (w); 1318 (s); 1282 (s); 1249 (m); 1163 (w); 1140 (m); 1118 (w); 1037 (m); 1004 (s) (W=O); 892 (m); 858 (m); 773 (w); 740 (s); 703 (m) cm$^{-1}$.

The compound is completely soluble in aliphatic, cycloaliphatic, aromatic and chlorinated hydrocarbons, such as n-heptane, cyclohexane, cyclopentene, benzene, chlorobenzene. The solutions do not show any signs of decomposition, even after a 1-month period of storage at room temperature.

EXAMPLE 3

Preparation of $WOCl_4$ . adiponitrile.
12.2 g of $WOCl_4$ = 35 millimoles
100 ml of anhydrous benzene distilled on $CaH_2$
3.8 ml of adiponitrile = 35 millimoles
are introduced into a 250 ml necked test tube, in a nitrogen atmosphere, at room temperature.

The mixture is reacted at room temperature for 20 hours under stirring. Thereupon the insoluble parts are filtered, 100 ml of petroleum ether are admixed to the mother solution and the whole is cooled down to 0°C. A brown compound crystallizes. It is washed with petroleum ether and then dried under vacuum by means of a mechanical pump.

Yield = 8.5 g (51%). The compound has the structure of $WOCl_4$ . adiponitrile, such structure being established by the elemental analysis and the infrared spectrum.

The infrared analysis shows a band at 2320 cm$^{-1}$ of the complexed nitrile and a band at 1003 cm$^{-1}$ corresponding to the W = O bond.

Infrared bands : 2320 (m) (C = N); 1468 (w); 1416 (w); 1350 (w); 1003 (s) (W = O); 916 (w); 787 (w); 732 (w); 673 (w) cm$^{-1}$.

The compound is completely soluble in aliphatic, cycloaliphatic, aromatic and chlorinated hydrocarbons, such as n-heptane, cyclohexane, cyclopentene, benzene, chlorobenzene. Solutions thereof do not show signs in said solvents, of decomposition, even after a 1-month period of storage at room temperature.

EXAMPLE 4

171 mg (0.3 millimoles) of $WOCl_4$ . phthalodinitrile, or an equivalent amount of the mother solution resulting from the reaction of $WOCl_4$ with phthalodinitrile, prepared according to Example 1, are introduced, in a nitrogen atmosphere, into a 100 ml flask. 3ml of anhydrous benzene and 3 ml (28 millimoles) of pentene-2 are added thereto. To the solution thus obtained 1.2 millimoles of ethyl aluminum dichloride are admixed under intense stirring. Reaction is carried on for 2 hours at 20°C, then 1 ml of methanol is added.

The composition of the reaction mixture is determined by gas chromatography. In addition to benzene, methanol and catalyst residues, it comprises butene-2, pentene-2 and hexene-3 in an amount corresponding to 73% of the metathesis equilibrium.

EXAMPLE 5

Example 4 is repeated, except that 0.3 millimoles of $WOCl_4$ . adiponitrile as described in Example 3 (or a corresponding amount of the reaction mixture, containing the product resulting from the reaction of $WOCl_4$ and adiponitrile) are used.

The metathesis products revealed by gas chromatography (butene-2, pentene-2 and hexene-3) correspond to a metathesis equilibrium of 60%.

EXAMPLE 6

Example 4 is repeated, except that 0.3 millimoles of $WOCl_4$ . ethyl phthalate as described in Example 3 (or an equivalent amount of the reaction mixture comprising the reaction product of $WOCl_4$ and ethyl phthalate) is used as one catalyst-forming component. The metathesis products, as determined by gas chromatography (butene-2, pentene-2, hexene-3) correspond to a metathesis equilibrium of 40%.

EXAMPLE 7

0.3 millimoles of $WOCl_4$ . phthalodinitrile, prepared according to Example 1, are dissolved in 20 g of cyclopentene and 20 ml of benzene. 0.45 millimoles of ethyl aluminum dichloride are added thereto at room temperature under intense stirring. Polymerization is stopped after 6 hours and the whole is poured into 200 ml of methanol. The precipitated polymer is washed with methanol, separated and dried under vacuum at room temperature. 14 g of polypentenamer are obtained, corresponding to a 70% conversion.

Catalysts prepared from organometallic compounds of metals belonging to Groups I to IV of the Mendelyeev Periodic Systems other than organometallic Al compounds, and the reaction products of tungsten oxyhalides other than $WOCl_4$ with organic ligands other than those exemplified give results similar to those shown in illustrative examples 4–6 and 7 when used in the dismutation of aliphatic olefins or the conversion of cycloolefins to polyalkenamers when the olefin subjected to the action of the present metathesis catalysts contains from 2 to 30 carbon atoms.

We claim:

1. Catalysts for the metathesis of olefins and cycloolefins containing from 2 to 30 carbon atoms and prepared by mixing
   A. a catalyst-forming component which consists of a complex of a tungsten oxyhalide with (b) an organic ligand selected from the group consisting of phthalodinitrile, adiponitrile and ethyl phthalate, the molar ratio of (a) to (b) being from 1:0.5 to 1:10; with
   B. a catalyst-forming component which is an alkyl aluminium halide the molar ratio of (a) in component (A), the component (B), being from 1:1 to 1:5.

2. Catalysts according to claim 1, wherein the tungsten oxyhalide (a) is $WOCl_4$.

3. Catalysts according to claim 1, wherein the ratio of (a) to (b) used to obtain catalyst-forming component (A) is from 1:0.9 to 1:1.5.

4. Catalysts according to claim 1, wherein the molar ratio of (a) in catalyst-forming component (A) to catalyst-forming component (B) is from 1:1.8 to 1:2.2.

5. The process of preparing catalysts for the metathesis of olefins and cycloolefins which consists essentially of reacting a tungsten oxyhalide as such with an organic ligand selected from the group consisting of phthalodinitrile, adipontrile and ethyl phthalate in a molar ratio of the oxyhalide to ligand of 1:0.5 to 1:10, in an inert atmosphere in a reaction medium consisting of a hydrocarbon of chlorinated hydrocarbon solvent, and at a temperature of from −50°C to +50°C, until the tungsten oxyhalide is solubilized, to thereby form a complex, and mixing the oxyhalide ligand complex with an alkyl aluminum halide in an amount such that the molar ratio of tungsten oxyhalide to alkyl aluminum halide is from 1:1 to 1:5, to obtain the catalyst.

6. The process of claim 5, in which the catalyst is prepared in the presence of the olefin to be metathesized.

7. The process according to claim 6, in which the olefin is pentene-2.

8. The process according to claim 6, in which the olefin is cyclopentene.

9. The process of claim 5, in which the alkyl aluminum halide is ethyl aluminum dichloride.

* * * * *

UNITED STATES PATENT OFFICE
CERTIFICATE OF CORRECTION

Patent No. 3,956,178      Dated May 11, 1976

Inventor(s) Alberto GRECO et al

It is certified that error appears in the above-identified patent and that said Letters Patent are hereby corrected as shown below:

In the list of references cited, the third item should read

- - - 3,558,518 1/1971 Zuech et al - - -.

Claim 1, line 12,     after "(A)" the word "the" should be

- - - to - - -.

Claim 5, line 8,     the word "of" before "chlorinated" should be - - - or - - -.

Signed and Sealed this

Seventh Day of March 1978

[SEAL]

Attest:

RUTH C. MASON      LUTRELLE F. PARKER
Attesting Officer      Acting Commissioner of Patents and Trademarks